United States Patent [19]

Pietsch et al.

[11] 4,221,214

[45] Sep. 9, 1980

[54] SUPPORTING BANDAGE

[75] Inventors: Hanns Pietsch, Hamburg; Dietrich Schulte, Pinneberg; Gunther Sachau, Norderstedt; Jurgen C. Quandt, Uetersen, all of Fed. Rep. of Germany

[73] Assignee: Biersdorf Aktiengesellschaft, Hamburg, Fed. Rep. of Germany

[21] Appl. No.: 9,266

[22] Filed: Feb. 2, 1979

[30] Foreign Application Priority Data

Feb. 16, 1978 [DE] Fed. Rep. of Germany ........ 2806509

[51] Int. Cl.³ ............................................... A61F 5/04
[52] U.S. Cl. ..................................................... 128/90
[58] Field of Search ..................... 128/90, 91 A, 91 R; 106/111

[56] References Cited

U.S. PATENT DOCUMENTS

| 2,697,434 | 12/1954 | Rodman | 128/90 |
| 3,932,190 | 1/1976 | Smith | 128/91 R |
| 4,100,242 | 7/1978 | Leach | 106/111 |

FOREIGN PATENT DOCUMENTS

| 167596 | 6/1954 | Australia | 128/90 |
| 224813 | 1/1959 | Australia | 128/90 |

*Primary Examiner*—C. Fred Rosenbaum
*Attorney, Agent, or Firm*—Bierman & Bierman

[57] ABSTRACT

A bandage for forming a stiffening or supporting cast comprising a carrier material and a composition thereon. The material includes a gas permeable flexible fabric-like base of the usual kind. The composition comprises (a) 55–97% by weight of gypsum, burnt, (b) 1–30%, preferably 3–30%, by weight of a highly cross-linked, finely dispersed poly-vinyl ester powder, which powder is more than 50% insoluble in ethyl-acetate, and (c) 0–12%, preferably 3–12%, by weight of a light weight cellular or porous filler having a bulk density of up to 0.1 g/cc.

18 Claims, No Drawings

SUPPORTING BANDAGE

This application claims the priority of German Application P 28 06 509.0, filed Feb. 16, 1978.

The present invention is directed to a bandage comprising broadly a flexible carrier with a hardenable gypsum-like material applied thereto. Such bandages are in general well known in the art and are used for the formation of casts applied to broken limbs and the like.

The composition is preferably mixed with a volatile organic solvent to form a paste. This paste is then spread on the carrier material and permitted to dry. If desired, heat may be applied in order to hasten the drying process. Alternatively, the material may be sprinkled on the carrier directly. The presence of a binder in the composition will, on the application of heat, aid in the adherence of the material to the carrier.

The bandage, prepared as above, is wet with water and applied to the body of the patient. In its moist and softened state, it is readily moldable to the shape desired. Since the hydration process is normally exothermic, it is desirable that, although setting take place as rapidly as possible, the amount of heat generated be limited so as not to injure the patient. Upon setting, the cast is formed and will remain on the patient until removed.

Many such compositions for spreading on the carrier are known. Most are based on gypsum. However, there are others based on synthetic materials. The latter are hardened by polymerization, condensation, or evaporation of softening solvents subsequent to the application of the bandage to the patient. The gypsum materials set, of course, merely by the addition of water.

Such casts, while generally satisfactory, suffer from certain important drawbacks. Primarily, they are extremely heavy, and hence awkward to wear. This is particularly true when the patient is a small child or an animal. For best results, a cast of this nature should be as light as possible, have good molding capacity, be compatible with the skin, be very insensitive to water, and also be quite stable. Attempts have been made to meet these various requirements by the use of various monomeric and polymeric substances. These have been added to the composition in dissolved, emulsified, or even in dried form. However, none of these prior art attempts have been successful in meeting all of the desired characteristics. There is a definite need for a bandage of this type which will maintain the desirable characteristics of the gypsum composition, i.e. good moldability and good compatibility with the skin, but will substantially improve the strength characteristics of the gypsum-based compositions (particularly as to impact and flexural strength), while also being substantially lighter than known materials.

The present invention is intended to meet these requirements. In accordance therewith, the bandage comprises the usual carrier material having a novel composition applied thereto. The composition comprises:

(a) 55-97% by weight of burnt gypsum;
(b) 1-30%, preferably 3-30%, by weight of a highly cross-linked, finely dispersed vinyl ester powder, such powder being more than 50% insoluble in ethyl acetate;
(c) 0-12%, preferably 3-12%, by weight of a light weight cellular or porous filler having a bulk density of up to 0.1 g/cc. Of course, the usual other additives or auxiliaries may also be included.

The gypsum component of the mixture is preferably the fast setting burnt gypsum which is generally available as gypsum hemihydrate. The requirement of good molding ability is obtained by maintaining a good degree of fineness of the product.

Since the setting of gypsum is an exothermic process, one should select those types of gypsum wherein the heat generated is given off slowly, even though the setting time is quite short. This will prevent injury to the skin.

The selection of the polymer powder of component (b) is of primary importance to the present invention. It is necessary that highly cross-linked polyvinyl esters in powder form with a maximum particle size of about $200\mu$ be used. This degree of cross-linkage is measured by the percentage of this material which is insoluble in the ethyl acetate. Such materials are readily redispersable in water, increase the flexural and impact strength to the desired extent, and increase the resistance of the set gypsum mixture to the action of moisture.

For this component, it is preferable to use highly cross-linked copolymers of vinyl acetate and vinyl esters of higher carboxylic acids. Particularly preferred, are copolymers of vinyl acetate and vinyl esters of versatic ® acids. Cross-linking, in both the preferred and general embodiments, is obtained in the usual manner with known difunctional compounds, preferably acrylic acid esters with divalent alcohols such as glykole or butandiole-1.4.

In the case of the preferred embodiments, it is particularly desirable that the degree of cross-linkage should be such that at least 60%, and preferably approximately 65%, of this polymer should be insoluble in ethyl acetate.

As a result of the present invention, the impact strength of the set gypsum material is increased up to 100% of that of gypsum alone. The increase of flexural strength is up to 25% of gypsum alone. As a result of the improved strength characteristics, a corresponding reduction in the thickness (and hence the weight) of the cast can be readily obtained. If a slightly cross-linked polymer is used, the impact strength can be increased by a maximum of 20%, and the flexual strength by a maximum of 6%. Thus, it is an important feature of the present invention that the polymer be highly cross-linked.

Further improvement in the characteristics in the cast may be obtained by the addition of light fillers. These are products having a bulk density of up to 0.1 g/cc. Obviously, it is important that the lowering of density by these fillers be maintained when the gypsum has been set in place. It has been found that fillers which produce low density by, for example, a fibrous striated or star-shaped structure are not suitable for the purposes of the present invention. The setting of the gypsum involves the growth of crystal needles, which thicken and penetrate into such fillers and thereby prevent them from achieving their desired density-lowering effect. For this reason, the fillers preferred, whether they be organic or inorganic, are those which produce lightness by a cellular or hollow spherical structure. In addition, they should have sufficient mechanical stability so that their structure is maintained even after processing. In addition, they must, of course, be insoluble in the organic dispersing agent used for application of the composition to the carrier.

The character of the fillers can be varied fairly widely, subject to the foregoing criteria. Hollow beads or cells of numerous raw materials may be used, provided that they are compatible with the skin and are physiologically acceptable, show no interfering interaction with the vinyl ester powder and the gypsum, and do not impair the good processability of the composition as a whole.

Hollow glass balls with a preferable particle diameter of about 50 to 150 microns have been found particularly suitable. Similar polyurethane or polyurea balls are also extremely suitable.

In addition to the foregoing, the filler can also be composed of, for example, polyolefins; such as polyethylene, polypropylene, polyisobutylene, and copolymers thereof; polyvinyl compounds; such as acrylic acid derivatives, vinylidene-acrylonitrile copolymers, polystyrene or styrene butadiene-block copolymers; polyamides; and certain high molecular weight natural products; such as cellulose and its derivatives. In addition, inorganic products, such as perlite, which is a loose powder of volcanic origin, or hollow quartz beads are also suitable.

It is preferable that the hollow beads or cellular materials of the filler should have a waterproof outer surface. This prevents the absorption of water when the bandages are wet prior to application. As a result, the drying time of the plastic cast is kept to a minimum. It is also desirable that the fillers not swell or dissolve in the organic dispersing agents used for the production of the coated bandages.

The addition of the fillers reduces the density of the overall gypsum mixture, but such addition will tend to reduce the impact and flexural strength of the cast. The reduction in strength is substantially a linear function of the reduction of the density. Such negative effects are offset to a substantial degree by the addition of the vinyl esters of the present invention. Therefore, a mechanically stable and very light air permeable plastic casts in accordance with the present invention can be obtained after hardening. Such casts will equal the standard commercial plastic casts in mechanical properties, but will have up to 40% lower density. It is not possible to obtain this result unless the parameters of the present invention are followed.

As previously stated, the nature of the carrier material is known in the art. However, it has been determined that mull, a thin, soft muslin, is particularly suitable. However, it is clear that the nature of this material can vary widely, as is known in the art. The primary desirable characteristics are flexibility and permeability to gases, especially air and steam. It is, of course, of particular advantage to the patient that the cast be capable of "breathing" to permit maximum comfort.

The usual additional substances may be incorporated in the compositions of the present invention, in similar manner to that known in the prior art. Such substances are frequently introduced as processing aids or assistants. For example, binders; such as polyvinyl alcohol, gelatin, dextrin, starch, tragacanth, carboxymethyl cellulose, and other cellulose derivatives; dispersing agents; such as polyvinyl pyrrolidone or polyoxyethylene triglyceride; wetting agents; dyes; thickeners; disinfectants; and setting accelerators for gypsum, are all suitable and acceptable additives to the compositions of the present invention.

Most of the foregoing are self explanatory, and persons of ordinary skill in the art will understand their purpose. Dispersing agents, for example, keep the mixture homogeneously distributed in the solvent prior to application to the carrier, and also prevent the premature setting of the gypsum or swelling of the fillers.

The bandages are produced by application of the powder to the carrier material. This can be done by sprinkling the composition onto the supporting material. However, it is preferred to first mix the dry composition with a highly volatile organic anhydrous solvent in order to form a thick paste or dispersion. This paste or dispersion is then spread on the carrier material and allowed to dry. For best results, moderate heat can be applied in order to speed up the evaporation. The binder will aid in fixing the mixture on the carrier after evaporation of the solvent.

The following examples are intended to illustrate the invention more fully, and to evidence their advantageous properties and compare them with the prior art. In these examples, the gypsum compositions were mixed with water and introduced into molds to produce bars of 12 cm length, 1.5 cm width, and 1.0 cm height after hardening. These are standard DIN bars of 18 cc volume. The bars were weighed after hardening, and the density was calculated from the weight and volume.

In order to test the mechanical strength of the bars, the impact strength was determined in accordance with DIN 53453, and the flexural strength was determined in accordance with DIN 53452.

EXAMPLES 1-6 AND COMPARISON EXAMPLE A

Various mixtures of pure burnt gypsum, manufactured by Merck, were blended with highly cross-linked polyvinyl ester dispersion powders. These powders were 65% insoluble in ethyl acetate. The blends were stirred with 100 ml water each and processed in accordance with the foregoing to the standard DIN bars. After drying and hardening, the impact strength, flexural strength and density were measured and determined. The value reported is the average of 5 measurements. The results of the foregoing tests are set forth in Table 1.

Table 1

| ex. | gypsum (g) | PVA powder* (g) | Impact strength (J/m$^2$) | flexural strength (N/mm$^2$) | density (g/cc) |
|---|---|---|---|---|---|
| 1 | 155.2 97% | 4.8 3% | 550 | 5.05 | 1.227 |
| 2 | 150.4 94% | 9.6 6% | 621 | 4.83 | 1.165 |
| 3 | 145.6 91% | 14.4 9% | 711 | 4.69 | 1.15 |
| 4 | 140.8 88% | 19.2 12% | 834 | 4.46 | 1.093 |
| 5 | 128.0 80% | 32.0 20% | 984 | 4.01 | 1.041 |
| 6 | 112.0 70% | 48.0 30% | 1046 | 3.06 | 0.94 |
| A | 160.0 100% | 0 0% | 540 | 4.16 | 1.199 |

*copolymer of vinyl acetate and vinyl esters of versatic ® acids

Comparison Examples B-F

Bars were produced from burnt gypsum and polyvinyl acetate dispersion powder in the same manner as set forth in Examples 1 to 6. However, instead of the highly cross-linked polyvinyl ester of the present invention, a product cross-linked to a lesser degree was used. The tests were carried out in the same manner as Examples 1 to 6 and demonstrate that these polymers strengthen the gypsum to a substantially lesser extent. The results of these tests are set forth in Table 2.

Table 2

| example | gypsum (g) | PVA powder (g) | impact strength (J/m$^2$) | flexural strength (N/mm$^2$) |
|---|---|---|---|---|
| B | 152 95% | 8 g A 5% | 555 | 4.41 |
| C | 144 90% | 16 g A 10% | 539 | 3.81 |
| D | 128 80% | 32 g A 20% | 621 | 3.70 |
| E | 144 90% | 16 g B 10% | 531 | 3.97 |
| F | 120 75% | 40 g B 25% | 670 | 3.27 |

A = polyvinyl acetate dispersion powder with 35% insoluble portion
B = polyvinyl acetate dispersion powder with 41.5% insoluble portion

EXAMPLES 7 TO 17

The basic gypsum-polyvinyl ester mixture was produced in accordance with Examples 1 to 6. Hollow polyurethane beads having a bulk density of 0.02 g/cc, as well as hollow glass balls, having a bulk density of 0.082 g/cc were added to the mix. The samples were handled and tested in the same manner as set forth in Examples 1 to 6. However, in Examples 11 and 12, 120 and 130 ml of water, respectively, were added during the mixing in place of the usual 100 ml. The results of these tests are set forth in Table 3.

Table 3

| ex. | gypsum (g) | PVA powder* (g) | PU-filler (g) | density (g/cm$^3$) | impact strength (J/m$^2$) |
|---|---|---|---|---|---|
| 7 | 140.8 88% | 9.6 6% | 9.6 6% | 0.703 | 329 |
| 8 | 137.6 86% | 11.2 7% | 11.2 7% | 0.652 | 589 |
| 9 | 116.8 73% | 32.0 20% | 11.2 7% | 0.602 | 850 |
| 10 | 100.8 63% | 48.0 30% | 11.2 7% | 0.576 | 1128 |
| 11 | 123.2 77% | 24.0 15% | 12.8 8% | 0.572 | 703 |
| 12 | 112.0 70% | 32.0 20% | 16.0 10% | 0.469 | 866 |

| | | | hollow glass balls (g) | | |
|---|---|---|---|---|---|
| 13 | 140.8 88% | 9.6 6% | 9.6 6% | 0.827 | 583 |
| 14 | 146.0 90% | 1.6 1% | 14.4 9% | 0.788 | 563 |
| 15 | 141.6 88.5% | 4.0 2.5% | 14.4 9% | 0.773 | 582 |
| 16 | 137.6 86% | 8.0 5% | 14.4 9% | 0.764 | 627 |
| 17 | 131.2 82% | 14.4 9% | 14.4 9% | 0.760 | 605 |

*copolymer of vinyl acetate and vinyl esters of versatic ® acids

Comparison Examples G-L

These examples are analagous to Examples 7 through 17, and contain both the gypsum and the filler, but eliminate the polyvinyl ester material. Otherwise, all measurements, etc, were carried out as in Examples 1 to 6. The results of these tests, as compared with Examples 7 to 17, indicate that the density is greatly reduced by the presence of these light fillers. However, the impact strength and flexural strength are substantially impaired thereby. The results of these Comparison Examples are set forth in Table 4. As can be seen from a comparison of Table 3 with Table 4, the compositions of the present invention (Table 3) have substantially higher impact strength than those outside the invention (Table 4).

Table 4

| example | gypsum (g) | filler (g) | density (g/cm$^3$) | impact strength (J/m$^2$) |
|---|---|---|---|---|
| G | 155.2 97% | 4.8 g C 3% | 0.918 | 474 |
| H | 150.4 94% | 9.6 g C 6% | 0.730 | 368 |
| I | 145.6 91% | 14.4 g C 9% | 0.534 | 302 |
| J | 140.8 88% | 19.2 g C 12% | 0.432 | 270 |
| K | 150.4 94% | 9.6 g D 6% | 0.913 | 424 |
| L | 145.6 91% | 14.4 g E 9% | 0.849 | 305 |

C = hollow polyurethane beads powder (bulk density 0.02)
D = perlite K 1f - inorganic loose powder of volcanic origin (bulk density 0.055)
E = hollow glass balls (bulk density 0.082)

EXAMPLES 18 TO 27 AND COMPARISON EXAMPLES M TO O

The standard bars were produced as described in Examples 1 to 6. After hardening, determinations were made of the resistance to water of the various samples. The bars were placed, as in thin-layer chromatography, in a glass chamber having 1 cm of water in the bottom. The height of the rise of water per unit time was measured and is set forth in Table 5.

Table 5

| example | gypsum (%) | PU (%) | PVA* (%) | auxiliary subst.(%) | mixture/H$_2$O (g) | height of rise (cm) | time (h) | velocity of rise (cm/h) |
|---|---|---|---|---|---|---|---|---|
| 18 | 85.3 | 7 | 7 | 0.7[1] | 160/140 | 7.5 | 6 | 1.25 |
| 19 | 86 | 10 | 3 | 1[2] | 160/140 | 10 | 3.5 | 2.9 |
| 20 | 79.5 | 10 | 10 | 0.5[3] | 160/140 | 1 | 6 | 0.16 |
| 21 | 81 | 7 | 10 | 2[4] | 160/110 | 3 | 6 | 0.5 |
| 22 | 86.5 | 3 | 10 | 0.5[3] | 160/100 | 5.5 | 6 | 0.92 |
| 23 | 73 | 7 | 20 | — | 160/100 | 2 | 6 | 0.33 |
| 24 | 63 | 7 | 30 | — | 160/100 | 0 | 6 | 0 |
| 25 | 97 | 0 | 3 | — | 160/100 | 0 | 2.33 | 4.29 |
| 26 | 91 | 0 | 9 | — | 160/100 | 10 | 6 | 1.6 |
| 27 | 88 | 0 | 12 | — | 160/100 | 2 | 6 | 0.33 |
| M | 97 | 3 | 0 | — | 160/100 | 10 | .5 | 6.67 |
| N | 91 | 9 | 0 | — | 160/140 | 10 | 0.75 | 13.33 |

Table 5-continued

| example | gypsum (%) | PU (%) | PVA* (%) | auxiliary subst.(%) | mixture/H$_2$O (g) | height of rise (cm) | time (h) | velocity of rise (cm/h) |
|---|---|---|---|---|---|---|---|---|
| O | 88 | 12 | 0 | — | 160/160 | 10 | 0.80 | 12.5 |

[1] polyoxyethylensorbitanmonooleate
[2] polyvinyl pyrrolidone
[3] Na-silicate
[4] Ca-sulfate . 2H$_2$O
*copolymer of vinyl acetate and vinyl esters of versatic® acids From the foregoing, it can be seen that the water resistance characteristic of the hardened material of the present invention is substantially better than that of the prior art. It is clear that the present invention produces casts which are substantially lighter in weight, while maintaining the other desirable characteristics of the pure gypsum compositions. The present invention is to be broadly construed, and not to be limited except by the character of the claims appended hereto.

What is claimed:

1. A bandage for forming a stiffening and/or supporting cast comprising a carrier material comprising a flexible fabric and a composition on said material, said composition comprising
   (a) 55–97% by weight burnt gypsum,
   (b) 1–30%, preferably 3–30%, by weight of a finely dispersed vinyl ester polymer powder, said powder being more than 50% insoluble in ethyl acetate, and
   (c) 0–12%, preferably 3–12%, by weight of a light weight cellular or porous filler having a bulk density of up to 0.1 g/cc.
2. A bandage according to claim 1 wherein said powder is polyvinyl acetate.
3. A bandage according to claim 1 wherein said powder is a copolymer of vinyl acetate and vinyl ester of higher carboxylic acid.
4. A bandage according to claim 1 wherein said powder is a copolymer of vinyl acetate and vinyl esters of versatic® acids.
5. A bandage according to claim 1 wherein said powder is at least 60% insoluble in ethyl acetate.
6. A bandage according to claim 5 wherein said powder is about 65% insoluble in ethyl acetate.
7. A bandage according to claim 1 wherein said filler is in the form of hollow beads.
8. A bandage according to claim 1 wherein said filler is taken from the class consisting of polyurethanes, polyureas polyolefins, polyvinyls, polystyrenes or styrene-butadiene copolymers, polyamides, high molecular weight natural products, glass, perlite and quartz.
9. A bandage according to claim 8 wherein said filler is taken from the class consisting of polyurethane, polyurea, polyethylene, polypropylene, polyisobutylene, and copolymers thereof, acrylic acid derivatives, vinylidene-acrylonitrile copolymers, polystyrene, and styrene-butadiene-block copolymers, cellulose and its derivatives, perlite, and hollow glass or quartz beads.
10. A bandage according to claim 1 wherein said composition further comprises at least one additive taken from the class consisting of binders, dispersing agents, wetting agents, dyes, thickeners, disinfectants, and setting accelerators for said gypsum.
11. A bandage according to claim 10 wherein said binders are taken from the class consisting of polyvinyl alcohol, gelatin, dextrin, starch, tragacanth, carboxymethyl cellulose and other cellulose derivatives.
12. A bandage according to claim 10 wherein said dispersing agents are taken from the class consisting of polyvinyl pyrrolidone and polyoxyethylene triglyceride.
13. A bandage according to claim 1 wherein said material is muslin.
14. A bandage according to claim 5 wherein said powder is a copolymer of vinyl acetate and vinyl esters of higher carboxylic acids.
15. A bandage according to claim 14 wherein said higher vinyl esters are versatic acid esters and said esters are cross-linked with difunctional compounds.
16. A bandage according to claim 15 wherein said copolymer is about 65% insoluble in ethyl acetate.
17. A bandage according to claim 1 wherein said material is permeable to steam and air.
18. A bandage according to claim 1 wherein said material is inelastic or partially elastic.

* * * * *